US010919907B2

(12) United States Patent
Park et al.

(10) Patent No.: US 10,919,907 B2
(45) Date of Patent: Feb. 16, 2021

(54) ANHYDROUS SUGAR ALCOHOL FLAKES AND MANUFACTURING METHOD THEREFOR

(71) Applicant: SAMYANG CORPORATION, Seoul (KR)

(72) Inventors: Hyuk Min Park, Incheon (KR); Hoon Ryu, Daejeon (KR); Jun Seop Im, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 16/651,540

(22) PCT Filed: Sep. 20, 2018

(86) PCT No.: PCT/KR2018/011149
§ 371 (c)(1),
(2) Date: Mar. 27, 2020

(87) PCT Pub. No.: WO2019/066385
PCT Pub. Date: Apr. 4, 2019

(65) Prior Publication Data
US 2020/0262841 A1 Aug. 20, 2020

(30) Foreign Application Priority Data
Sep. 28, 2017 (KR) .......... 10-2017-0126191

(51) Int. Cl.
C07D 493/04 (2006.01)
(52) U.S. Cl.
CPC ............... *C07D 493/04* (2013.01)
(58) Field of Classification Search
CPC ................... C07D 493/04

USPC .......... 549/464
See application file for complete search history.

(56) References Cited

U.S. PATENT DOCUMENTS

| 9,163,031 B2 | 10/2015 | Ibert et al. |
| 9,505,777 B2 | 11/2016 | Ryu et al. |
| 2013/0281718 A1 | 10/2013 | Ibert et al. |
| 2015/0299216 A1 | 10/2015 | Ryu et al. |

FOREIGN PATENT DOCUMENTS

| EP | 0 308 892 A2 | 3/1989 | |
| KR | 10-1989-0005909 A | 5/1989 | |
| KR | 10-1079518 B1 | 11/2011 | |
| KR | 10-2012-0066904 A | 6/2012 | |
| KR | 10-2013-0121825 A | 11/2013 | |
| KR | 102013-0121825 A * | 11/2013 | ............... B01J 2/02 |
| KR | 10-2014-0047842 A | 4/2014 | |
| KR | 10-2014-0105186 A | 9/2014 | |
| KR | 10-1631580 B1 | 6/2016 | |
| KR | 10- 701254 B1 | 2/2017 | |
| KR | 10-2017-0078508 A | 7/2017 | |
| KR | 10-1890660 B1 | 8/2018 | |

OTHER PUBLICATIONS

International Search Report (PCT/ISA/210) issued in PCT/KR2018/011149, dated Jan. 3, 2019.

* cited by examiner

*Primary Examiner* — Nizal S Chandrakumar
(74) *Attorney, Agent, or Firm* — Birch, Stewart, Kolasch & Birch, LLP

(57) ABSTRACT

The present invention relates to anhydrous sugar alcohol flakes and a manufacturing method therefor and, more specifically, to a particular form of anhydrous sugar alcohol flakes capable of preventing or mitigating caking occurring during the storage of products, and to a manufacturing method therefor.

8 Claims, No Drawings

ANHYDROUS SUGAR ALCOHOL FLAKES AND MANUFACTURING METHOD THEREFOR

TECHNICAL FIELD

The present invention relates to anhydrosugar alcohol flakes and a method for preparing the same, and more specifically, anhydrosugar alcohol flakes in a particular form capable of preventing or reducing the caking phenomenon occurring during the product storage and a method for preparing the same.

BACKGROUND ART

Hydrogenated sugar (also referred to as "sugar alcohol") means a compound obtained by adding hydrogen to the reductive end group in sugar, and generally has a chemical formula of $HOCH_2(CHOH)_nCH_2OH$ wherein n is an integer of 2 to 5. According to the number of carbon atoms, hydrogenated sugar is classified into tetritol, pentitol, hexitol and heptitol (4, 5, 6 and 7 carbon atoms, respectively). Among them, hexitol having 6 carbon atoms includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, patch adhesive, medicaments such as mouthwash, etc., solvents for compositions in the cosmetics industry, emulsifiers in the food industry, etc. In addition, it can increase the glass transition temperature of polymer materials like polyester, PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer.

Among the products of anhydrosugar alcohol, the conventional products in a powder from or pellet form (for example, Korean Laid-open Patent Publication No. 10-2013-0128125) may cause the caking phenomenon due to the compression by external force during storage or due to the melting during storage in atmosphere at high temperature and then cooling. The caking phenomenon causes an extra process and time to break down the caky product at the time of using the product, and in addition, it may decrease the working efficiency due to the concern about the safety and labor of workers in such an extra process.

Problems to be Solved

The present invention is intended to resolve the above-stated problems of the prior arts, and has an object of providing anhydrosugar alcohol flakes in a form capable of preventing or reducing the caking phenomenon occurring during the product storage and thereby increasing the working efficiency and decreasing the production cost, and a method for preparing the same.

Technical Means

In order to resolve the above-stated problems, the present invention provides an anhydrosugar alcohol flake product which is a collective matter of plural anhydrosugar alcohol flakes, wherein the plural anhydrosugar alcohol flakes have an average thickness of from 0.5 mm to 4.5 mm, and 90% by weight or more of the anhydrosugar alcohol flakes have the major axis in a length of 5 mm or greater.

In another aspect, the present invention provides a method of making an anhydrosugar alcohol flake product which is a collective matter of plural anhydrosugar alcohol flakes, the method comprising the step of: (1) feeding a liquid of melted anhydrosugar alcohol continuously to a cooling plate of a flaker; (2) cooling the liquid of melted anhydrosugar alcohol in the cooling plate into a sheet form while moving the cooling plate; (3) separating the cooled anhydrosugar alcohol in sheet form from the cooling plate by using a blade installed at the exit of the cooling plate; and (4) passing the separated anhydrosugar alcohol in sheet form through a pulverizer to obtain plural anhydrosugar alcohol flakes, wherein the plural anhydrosugar alcohol flakes have an average thickness of from 0.5 mm to 4.5 mm, and 90% by weight or more of the anhydrosugar alcohol flakes have the major axis in a length of 5 mm or greater.

Effect of the Invention

The anhydrosugar alcohol flake product according to the present invention has a lower apparent specific gravity as compared with conventional anhydrosugar alcohol products in a powder from or pellet form, and thus it can reduce or eliminate the caking phenomenon due to the compression by external force during storage or due to the melting during storage in atmosphere at high temperature and then cooling. Through this, at the time of using the product, the time to feeding it into the process can be reduced and an extra process and time to break down the caky product at the time of using the product can be reduced or eliminated. In addition, there is little or no concern about the safety and labor of workers in such an extra process, and thereby the working efficiency can be improved.

CONCRETE MODE FOR CARRYING OUT THE INVENTION

The present invention is explained in more detail below.

The anhydrosugar alcohol flake product of the present invention is a collective matter of plural anhydrosugar alcohol flakes, wherein the plural anhydrosugar alcohol flakes have an average thickness of from 0.5 mm to 4.5 mm, and 90% by weight or more of the anhydrosugar alcohol flakes have the major axis in a length of 5 mm or greater.

In an embodiment, the average thickness of the plural anhydrosugar alcohol flakes may be 0.5 mm or greater, 0.6 mm or greater, 0.7 mm or greater or 0.8 mm or greater, and it may be 4.5 mm or less, 4.4 mm or less, 4.3 mm or less, 4.2 mm or less, 4.1 mm or less or 4.0 mm or less.

In an embodiment, in the anhydrosugar alcohol flakes, 90% by weight or more, 91% by weight or more, 92% by weight or more, 93% by weight or more, 94% by weight or more, 95% by weight or more or 96% by weight or more thereof, and 100% by weight or less, 99% by weight or less, 98% by weight or less or 97% by weight or less thereof may have the major axis in a length of 5 mm or greater. The upper limit of the length of the major axis of the anhydrosugar alcohol flake may vary according to the concrete equipment, and for example, the length of the major axis may be 10 mm or less or 8 mm or less, but it is not limited thereto.

In an embodiment, the apparent specific gravity (ton/m$^3$) of the anhydrosugar alcohol flake product of the present invention may be 0.8 or less, 0.75 or less, 0.7 or less, 0.65 or less, 0.6 or less or 0.55 or less, and it may be 0.3 or greater, 0.35 or greater, 0.4 or greater or 0.45 or greater. As described herein, "apparent specific gravity" means the weight of anhydrosugar alcohol flake filled in a 1 m$^3$-volume package (i.e., weight (ton) of anhydrosugar alcohol flake per cubic meter (m$^3$) (ton/m$^3$)).

In an embodiment, according to applying external force, the anhydrosugar alcohol flake product of the present invention may exhibit an increase of the apparent specific gravity (i.e., apparent specific gravity after applying external force–apparent specific gravity before applying external force) of 0.2 or less, and more concretely, 0.18 or less, 0.16 or less, 0.15 or less, 0.12 or less or 0.1 or less. The lower limit of the increase of the apparent specific gravity according to applying external force may be 0, or it may be 0.01 or 0.05, but there is no special limitation thereto. As described herein, "applying external force" means packaging 500 kg of the anhydrosugar alcohol flake product and storing it outdoors at a daily mean temperature of from 21° C. to 26° C. for 100 days under applied external force by 500 kg load thereon.

In an embodiment, according to applying external force, the anhydrosugar alcohol flake product of the present invention may exhibit an increase of the degree of retention (or discharge time) (i.e., degree of retention after applying external force–degree of retention before applying external force) of 5 minutes or less, and more concretely, 4 minutes or less, 3 minutes or less, 2 minutes or less or 1 minutes or less. The lower limit of the increase of the degree of retention according to applying external force may be 0, or it may be 10 seconds or 20 seconds, but there is no special limitation thereto. As described herein, "degree of retention (or discharge time)" means the time taken for completely discharging 500 kg of the anhydrosugar alcohol flake product from the package through a circular discharge hole with 20 cm diameter formed at the bottom of the package while tilting the package with the discharge hole to one side by 60°.

In an embodiment, after applying external force, the anhydrosugar alcohol flake product of the present invention may exhibit the degree of caking of 40% or less, 35% or less, 30% or less, 25% or less or 20% or less. The lower limit of the degree of caking after applying external force may be 0%, or it may be 1% or 2%, but there is no special limitation thereto. As described herein, "degree of caking" means, when the anhydrosugar alcohol flake product is packaged and stored under applied external force and then filtered with a sieve of 50 mm×50 mm, the weight ratio of the anhydrosugar alcohol flake product which cannot pass through the sieve and remains on the sieve [i.e., the weight of anhydrosugar alcohol flake remaining on the sieve (kg)/the total weight of the packaged anhydrosugar alcohol flake (kg) *100%].

The anhydrosugar alcohol flake product of the present invention can be prepared—after a process of converting hydrogenated sugar to anhydrosugar alcohol by dehydration reaction and a process of distilling the dehydration reaction product (or further after at least one purification process selected from crystallization, decolorization, ion exchange resin treatment and concentration after the distillation process)—by feeding a liquid of melted anhydrosugar alcohol to a flaker and obtaining it in flake form. In an embodiment, the anhydrosugar alcohol flake product of the present invention may have a purity of from 95 to 99.9% by weight, a UV transmittance (275 nm) of from 85 to 99%, a moisture content of from 0.1 to 5% by weight and a specific gravity of from 1.1 to 1.4 (or from 1.2 to 1.3) g/cm$^3$.

Therefore, another aspect of the present invention provides a method of making an anhydrosugar alcohol flake product which is a collective matter of plural anhydrosugar alcohol flakes, the method comprising the step of: (1) feeding a liquid of melted anhydrosugar alcohol continuously to a cooling plate of a flaker; (2) cooling the liquid of melted anhydrosugar alcohol in the cooling plate into a sheet form while moving the cooling plate; (3) separating the cooled anhydrosugar alcohol in sheet form from the cooling plate by using a blade installed at the exit of the cooling plate; and (4) passing the separated anhydrosugar alcohol in sheet form through a pulverizer to obtain plural anhydrosugar alcohol flakes, wherein the plural anhydrosugar alcohol flakes have an average thickness of from 0.5 mm to 4.5 mm, and 90% by weight or more of the anhydrosugar alcohol flakes have the major axis in a length of 5 mm or greater.

The flaker may be a disc type flaker, a drum type flaker or a belt type flaker, but it is not limited thereto.

According to an embodiment, the anhydrosugar alcohol flake product of the present invention can be prepared as follows:

i) A liquid of concentrated or melted anhydrosugar alcohol (for example, isosorbide)—which was prepared through a production process of anhydrosugar alcohol—is fed continuously to a cooling plate through a nozzle with a constant size. At this time, the liquid of melted anhydrosugar alcohol fed to the cooling plate may be at a temperature of from 60 to 90° C. If the temperature of the liquid of melted anhydrosugar alcohol is lower than 60° C., clogging of the feeding nozzle may happen. In contrast, if the temperature of the liquid of melted anhydrosugar alcohol is higher than 90° C., the liquid of melted anhydrosugar alcohol may not be sufficiently cooled on the cooling plate and accordingly it may be difficult to obtain the anhydrosugar alcohol in a sheet form with a uniform thickness. The flow rate of the liquid of melted anhydrosugar alcohol fed to the cooling plate may be controlled within a range of from 50 to 150 kg/hr (more concretely, from 60 to 150 kg/hr, and still more concretely, from 80 to 150 kg/hr).

ii) In order to prepare the anhydrosugar alcohol flake with a uniform size, the rotation speed of the cooling plate (disc type, drum type or belt type) may be controlled within a range of from 1 to 2 rpm. The temperature of the cooling plate may be controlled within a range of from 1 to 25° C. (more concretely, from 5 to 20° C., and still more concretely, from 5 to 15° C.).

iii) The cooled anhydrosugar alcohol in sheet form may be separated from the cooling plate through a blade installed at the exit of the cooling plate of the flaker.

iv) Then, the anhydrosugar alcohol in sheet form separated from the cooling plate may be pulverized by using a pulverizer. At this time, the rotation speed of the pulverizer may be controlled within a range of from 100 to 300 rpm. By controlling the rotation speed of the pulverizer within such a range, it is possible to obtain anhydrosugar alcohol flakes wherein 90% by weight or more thereof have the major axis in a length of 5 mm or greater.

In an embodiment, the production process of anhydrosugar alcohol may be explained as follows, but it is not limited thereto.

The anhydrosugar alcohol in the present invention may be prepared by a method comprising the steps of: (1) converting hydrogenated sugar to anhydrosugar alcohol by dehydration reaction; (2) distilling the resulting liquid of the reaction of said step (1); (3) crystallizing the resulting distillate of said step (2); (4) decolorizing the resulting crystallite of said step (3); (5) treating the resulting product of said step (4) with cation exchange resin; (6) treating the resulting product of said step (5) with anion exchange resin; and (7) concentrating the resulting product of said step (6).

The hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol having 6 carbons includes sorbitol, mannitol, iditol, galactitol, etc. and in particular, sorbitol and mannitol are very useful materials. The hydrogenated sugar for use is preferably hexitol, more preferably a hydrogenated sugar selected from sorbitol, mannitol, iditol and mixtures thereof, and even more preferably sorbitol which can be prepared easily through hydrogenation reaction of glucose derived from starch.

In the above step (1), the hydrogenated sugar is converted to anhydrosugar alcohol by dehydration reaction. It is preferable to use an acid catalyst in dehydrating hydrogenated sugar to convert it to anhydrosugar alcohol. According to an embodiment, for the acid catalyst, a single acid catalyst such as sulfuric acid, nitric acid, hydrochloric acid, p-toluenesulfonic acid, phosphoric acid, etc. can be used, and more preferably, sulfuric acid can be used. According to another embodiment, for the acid catalyst, an acid mixture of a first acid and a second acid can be used, and more preferably, sulfuric acid can be used as the first acid and one or more sulfur-containing acid materials selected from the group consisting of p-toluenesulfonic acid, methanesulfonic acid, ethanesulfonic acid, benzenesulfonic acid, naphthalenesulfonic acid and aluminum sulfate can be used as the second acid. In case of using an acid mixture, the weight ratio of the first acid:the second acid is preferably from 1:9 to 7:3. If this ratio is less than 1:9 (that is, if the amount of the first acid is relatively too little), the production rate of anhydrosugar alcohol may be lowered. If this ratio is greater than 7:3 (that is, if the amount of the first acid is relatively too much), the generation of sugar polymer may be increased. The acid catalyst is preferably used in an amount of from 0.5 to 10 parts by weight per 100 parts by weight of the hydrogenated sugar (e.g., hexitol). If the amount of acid catalyst is less than 0.5 part by weight per 100 parts by weight of the hydrogenated sugar, the conversion time to anhydrosugar alcohol may become excessively long. If the amount of acid catalyst is greater than 10 parts by weight, the generation of sugar polymer may be increased and the conversion rate may be lowered.

The step of converting hydrogenated sugar to anhydrosugar alcohol may be conducted in the presence of an acid catalyst as explained above, at a temperature of from 105° C. to 190° C. under a pressure of 1 to 100 mmHg for 1 hour to 10 hours, but it is not limited thereto. In the case of using an acid catalyst during the dehydration reaction of hydrogenated sugar, it is preferable to neutralize the reaction product liquid. After the dehydration reaction, the neutralization may be conducted by cooling the reaction product liquid (e.g., to 100° C. or lower) and adding thereto conventional alkali such as sodium hydroxide. The neutralized reaction product liquid preferably has a pH of 6 to 8. According to a preferable embodiment, the resulting liquid of the step of converting hydrogenated sugar to anhydrosugar alcohol may be pre-treated before being fed to the distilling step. The purpose of the pre-treatment is to remove moisture and a low-boiling-point substance(s) remaining in the resulting liquid of the converting step, and may be conducted by stirring the resulting liquid of the converting step conventionally at a temperature of from 90° C. to 110° C. under a pressure of 10 mmHg to 100 mmHg for 30 minutes or longer (e.g., 30 minutes to 4 hours), but it is not limited thereto.

Dianhydrohexitol—which is the dehydrated product of hexitol—is preferably obtained as the anhydrosugar alcohol—which is the product of said conversion reaction—and more preferably, the obtained anhydrosugar alcohol is selected from isosorbide (1,4-3,6-dianhydrosorbitol), isomannide (1,4-3,6-dianhydromannitol), isoidide (1,4-3,6-dianhydroiditol) and mixtures thereof. Among them, isosorbide is particularly useful for industrial and medicinal application.

In the above step (2), the distillation can be conducted at a temperature condition of preferably from 100° C. to 250° C., more preferably from 100° C. to 200° C., and still more preferably from 110° C. to 170° C., and under a pressure condition of preferably 10 mmHg or less (e.g., 0.0001 to 10 mmHg, more concretely 0.0001 to 8 mmHg), more preferably 5 mmHg or less (e.g., 0.001 to 5 mmHg), and still more preferably 1 mmHg or less (e.g., 0.01 to 1 mmHg, more concretely 0.01 to 0.8 mmHg). If the distillation temperature is lower than 100° C., the distillation of anhydrosugar alcohol may not be conducted effectively. If the distillation temperature is higher than 250° C., the purity of anhydrosugar alcohol may be lowered and the color will become dark, rendering decolorization difficult. If the distillation pressure is greater than 10 mmHg, the distillation temperature should be elevated in order to distill anhydrosugar alcohol and in such a case, the aforesaid problems may be generated. On the other hand, excessively low distillation pressure is not preferable since an extra cost would be necessitated for a high-vacuum device to reduce the distillation pressure and the distillation purity would be lowered. If necessary, the distillation may be conducted through two or more steps. There is no special limitation in the method and device for the distillation, and any conventionally known method and device in this field may be utilized as it is or with proper modification. For example, a general condenser-type evaporator or column distillator may be used, or a thin-film distillator may be utilized for the distillation.

In the above step (3), there is no special limitation in the method and device for the crystallization, and any conventionally known crystallization method and device in this field may be utilized as it is or with proper modification. For example, concretely, it is possible to use a method of dissolving anhydrosugar alcohol in a solvent such as water, ethyl acetate, acetone, toluene, benzene, xylene, alcohol, etc. at an elevated temperature if necessary, and then lowering the temperature of the solution to precipitate the anhydrosugar alcohol crystals, or a method of melt crystallization using no solvent may be used. In case of crystallization using solvent, the kind and amount of solvent used and the elevated/lowered temperature, etc. may be determined properly according to the processing capacity and concrete facility conditions, and the temperature condition of melt crystallization may also be determined properly. According to an embodiment, acetone is used as a solvent, and after the solvent and the anhydrosugar alcohol distillate are mixed with a weight ratio of from 10:1 to 1:1, the temperature of the solution is elevated to 30° C. or higher and then lowered to 0° C. to precipitate the anhydrosugar alcohol crystals, which are then separated from the mother liquid to obtain the crystallite.

In the above step (4), preferably, the decolorization can be conducted by contacting an aqueous solution, where the obtained crystallite of anhydrosugar alcohol is dissolved in water (for example, distilled water), with active carbon. At this time, the average particle size of the active carbon is preferably from 0.25 to 1.0 mm, and more preferably from 0.25 mm to 0.70 mm. If the active carbon particles are so small that the average particle size is less than 0.25 mm, in the case of decolorization on a column the problems of serious decrease of the flow rate and increase of the pressure in the column may result. On the other hand, if the active carbon particles are so large that the average particle size is greater than 1.0 mm, the problems of increase of the ion content and conductivity of the resulting anhydrosugar alcohol and increase of the color index may also result.

There is no special limitation in the manner of contacting the aqueous solution of anhydrosugar alcohol with active carbon. For example, the contact may be conducted in a manner of passing the aqueous solution of anhydrosugar alcohol through a column packed with the active carbon, or it may alternatively be conducted in a manner of incorporating the aqueous solution of anhydrosugar alcohol and the active carbon into a reactor and mixing them with agitation for a given time. According to a preferable embodiment, the decolorization is conducted in a manner of passing the aqueous solution of anhydrosugar alcohol through a column packed with the active carbon.

As the active carbon, one or more selected from active carbon groups obtained by activating a plant source such as wooden material, palm, etc. or a mineral source such as brown coal, bituminous coal, soft coal, anthracite coal, etc. may be used. There is no special limitation in the form of active carbon particle, and fine granular active carbon (e.g., average particle size of from 0.25 to 0.75 mm), granular active carbon (e.g., average particle size of 0.75 mm or greater), powder active carbon (e.g., average particle size of 0.25 mm or less), etc. may be used. According to an embodiment, fine granular active carbon is used. In order to increase the efficiency of the active carbon, pre-treated (e.g., washed) active carbon may be used.

In the above step (5), the cation exchange resin treatment may be accomplished by contacting the decolorized resulting liquid with cation exchange resin, and this may be conducted in a manner of passing the decolorized resulting liquid through a column packed with the ion exchange resin. As the cation exchange resin, all of strong cation exchange resin (e.g., TRILITE-SCR-B) and weak cation exchange resin (e.g., DIAION WK11) may be used, and strong cationic ion exchange resin is preferably used. As the strong cation exchange resin, one or more selected from H-form strong cation exchange resin (e.g., TRILITE-SCR-BH) and Na-form strong cation exchange resin (e.g., TRILITE-SCR-B) may be used preferably.

In the above step (6), the anion exchange resin treatment may be conducted in a manner of passing the resulting liquid of step (5) through a column packed with the anion exchange resin. As the anion exchange resin, all of strong anion exchange resin (e.g., TRILITE AMP24) and weak anion exchange resin (e.g., DIAION WA10) may be used, and strong anion exchange resin is preferably used. As the strong anion exchange resin, Cl-form strong anion exchange resin (e.g., TRILITE AMP24) may be used preferably.

In the above step (7), the concentration treatment may be conducted in a manner of heating the resulting liquid of said step (6) under vacuum condition by using a facility for concentration. The concentration may be conducted at a temperature condition of preferably from 60° C. to 120° C. and more preferably from 65° C. to 90° C., and under a vacuum condition of preferably −800 mbar or greater, more preferably −950 mbar or greater, and still more preferably −975 mbar or greater. If the concentration temperature is lower than 60° C., crystals may be generated during the concentration of anhydrosugar alcohol. If the concentration temperature is higher than 120° C., the purity of anhydrosugar alcohol may be lowered and the color will become dark, and thus a product with good quality cannot be obtained. If the vacuum condition for the concentration is lower than −800 mbar, a product with a moisture content of from 0.1 to 5% by weight cannot be obtained.

The present invention is explained in more detail through the following Examples and Comparative Examples. However, the scope of the present invention is not limited thereby in any manner.

EXAMPLES

Preparation Example 1: Preparation of Isosorbide Flakes

Isosorbide flakes were prepared by using a disc type flaker. First, a liquid of melted isosorbide (temperature of the melted liquid: 60° C. to 90° C.) was fed to a disc type cooling plate with a feeding flow rate of 50 to 150 kg/hr. Then, the disc type cooling plate was rotated at a rotation speed of 1 to 2 rpm while maintaining the temperature of the disc type cooling plate within a range of from 1 to 25° C. During the rotation of the disc type cooling plate, the liquid of melted isosorbide was cooled on the disc type cooling plate, and the cooled isosorbide in sheet form was separated through a blade installed at the exit of the disc type cooling plate. Then, passing through a pulverizer, the separated isosorbide in sheet form was pulverized into constantly-sized isosorbide flakes. At that time, the pulverizer was rotated at a rotation speed of 100 to 300 rpm to pulverize the separated anhydrosugar alcohol in sheet form.

Example 1: Preparation of Isosorbide Flakes with an Average Thickness of 0.8 mm

Isosorbide flakes were prepared in the same manner as that of Preparation Example 1. At that time, the liquid of melted isosorbide was fed to the disc type cooling plate with a feeding flow rate of 80 kg/hr, the rotation speed of the disc type cooling plate was maintained at 2 rpm, the temperature of the disc type cooling plate was maintained at 15° C., and the blade of the pulverizer was rotated at 100 rpm, to prepare isosorbide flakes. The prepared isosorbide flakes had an average thickness of 0.8 mm, and among the prepared isosorbide flakes, the amount of isosorbide flakes having the major axis in a length of 5 mm or greater was 91% by weight, based on the total isosorbide flakes.

500 kg of the prepared isosorbide flake product was packaged and stored outdoors at a daily mean temperature of from 21° C. to 26° C. (12° C. at the lowest, 40° C. at the highest) for 100 days under applied external force by 500 kg load thereon. Thereafter, the packaged isosorbide flake product was analyzed in terms of the apparent specific gravity, the degree of retention at the time of opening the package and the degree of caking, and the results are shown in Table 1 below.

Example 2: Preparation of Isosorbide Flakes with an Average Thickness of 2.5 mm Isosorbide flakes were prepared in the same manner as that of Preparation Example 1. At that time, the liquid of melted isosorbide was fed to the disc type cooling plate with a feeding flow rate of 120 kg/hr, the rotation speed of the disc type cooling plate was maintained at 1 rpm, the temperature of the disc type cooling plate was maintained at 10° C., and the blade of the pulverizer was rotated at 100 rpm, to prepare isosorbide flakes. The prepared isosorbide flakes had an average thickness of 2.5 mm, and among the prepared isosorbide flakes, the amount of isosorbide flakes having the major axis in a length of 5 mm or greater was 94% by weight, based on the total isosorbide flakes.

500 kg of the prepared isosorbide flake product was packaged and stored outdoors at a daily mean temperature of from 21° C. to 26° C. (12° C. at the lowest, 40° C. at the highest) for 100 days under applied external force by 500 kg load thereon. Thereafter, the packaged isosorbide flake product was analyzed in terms of the apparent specific gravity, the degree of retention at the time of opening the package and the degree of caking, and the results are shown in Table 1 below.

Example 3: Preparation of Isosorbide Flakes with an Average Thickness of 4 mm Isosorbide flakes were prepared in the same manner as that of Preparation Example 1. At that time, the liquid of melted isosorbide was fed to the disc type cooling plate with a feeding flow rate of 150 kg/hr, the rotation speed of the disc type cooling plate was maintained at 1 rpm, the temperature of the disc type cooling plate was maintained at 7° C., and the blade of the pulverizer was rotated at 100 rpm, to prepare isosorbide flakes. The prepared isosorbide flakes had an average thickness of 4 mm, and among the prepared isosorbide flakes, the amount of isosorbide flakes having the major axis in a length of 5 mm or greater was 96% by weight, based on the total isosorbide flakes.

500 kg of the prepared isosorbide flake product was packaged and stored outdoors at a daily mean temperature of from 21° C. to 26° C. (12° C. at the lowest, 40° C. at the highest) for 100 days under applied external force by 500 kg load thereon. Thereafter, the packaged isosorbide flake product was analyzed in terms of the apparent specific gravity, the degree of retention at the time of opening the package and the degree of caking, and the results are shown in Table 1 below.

Comparative Example 1: Preparation of Isosorbide Flakes with an Average Thickness of 0.4 mm Isosorbide flakes were prepared in the same manner as that of Preparation Example 1. At that time, the liquid of melted isosorbide was fed to the disc type cooling plate with a feeding flow rate of 40 kg/hr, the rotation speed of the disc type cooling plate was maintained at 2 rpm, the temperature of the disc type cooling plate was maintained at 29° C., and the blade of the pulverizer was rotated at 100 rpm, to prepare isosorbide flakes. The prepared isosorbide flakes had an average thickness of 0.4 mm, and among the prepared isosorbide flakes, the amount of isosorbide flakes having the major axis in a length of 5 mm or greater was 90% by weight, based on the total isosorbide flakes.

500 kg of the prepared isosorbide flake product was packaged and stored outdoors at a daily mean temperature of from 21° C. to 26° C. (12° C. at the lowest, 40° C. at the highest) for 100 days under applied external force by 500 kg load thereon. Thereafter, the packaged isosorbide flake product was analyzed in terms of the apparent specific gravity, the degree of retention at the time of opening the package and the degree of caking, and the results are shown in Table 1 below.

Comparative Example 2: Isosorbide Crystalline Powder 500 kg of isosorbide crystalline powder—which had an average thickness of less than 0.5 mm, and less than 1% by weight of the total crystalline powder had the major axis in a length of 5 mm or greater—was packaged and stored outdoors at a daily mean temperature of from 21° C. to 26° C. (12° C. at the lowest, 40° C. at the highest) for 100 days under applied external force by 500 kg load thereon. Thereafter, the packaged isosorbide flake product was analyzed in terms of the apparent specific gravity, the degree of retention at the time of opening the package and the degree of caking, and the results are shown in Table 1 below.

Comparative Example 3: Preparation of Isosorbide Flakes with an Average Thickness of 1 mm Isosorbide flakes were prepared in the same manner as that of Preparation Example 1. At that time, the liquid of melted isosorbide was fed to the disc type cooling plate with a feeding flow rate of 90 kg/hr, the rotation speed of the disc type cooling plate was maintained at 2 rpm, the temperature of the disc type cooling plate was maintained at 15° C., and the blade of the pulverizer was rotated at 500 rpm, to prepare isosorbide flakes. The prepared isosorbide flakes had an average thickness of 1 mm, and among the prepared isosorbide flakes, the amount of isosorbide flakes having the major axis in a length of 5 mm or greater was 60% by weight, based on the total isosorbide flakes.

500 kg of the prepared isosorbide flake product was packaged and stored outdoors at a daily mean temperature of from 21° C. to 26° C. (12° C. at the lowest, 40° C. at the highest) for 100 days under applied external force by 500 kg load thereon. Thereafter, the packaged isosorbide flake product was analyzed in terms of the apparent specific gravity, the degree of retention at the time of opening the package and the degree of caking, and the results are shown in Table 1 below.

TABLE 1

| | Flake Thickness (mm) | Amount of flakes having the major axis in a length of 5 mm or greater (% by weight) | Apparent specific gravity | | Degree of Retention (time) | | Degree of Caking (%) |
|---|---|---|---|---|---|---|---|
| | | | Before applying external force | After applying external force | Before applying external force | After applying external force | After applying external force |
| Example 1 | 0.8 | 91 | 0.72 | 0.88 | 4 min. 58 sec. | 8 min. 30 sec. | 20 |
| Example 2 | 2.5 | 94 | 0.58 | 0.73 | 4 min. 30 sec. | 5 min. 37 sec. | 7 |
| Example 3 | 4.0 | 96 | 0.50 | 0.60 | 3 min. 45 sec. | 4 min. 15 sec. | 4 |
| Comparative Example 1 | 0.4 | 90 | 0.81 | 1.07 | 5 min. 13 sec. | Discharging impossible | 64 |
| Comparative Example 2 | Powder (less than 0.5) | Less than 1 | 0.84 | 1.13 | 5 min. 10 sec. | Discharging impossible | 90 |
| Comparative Example 3 | 1 | 60 | 0.69 | 0.91 | 4 min. 52 sec. | Discharging impossible | 44 |

[Methods for Measurement]

1. Apparent specific gravity: The weight (ton) of isosorbide flake filled in a 1 m³-volume package (i.e., Tons of isosorbide flake/1 m³) was measured.

2. Degree of retention: The time taken for completely discharging 500 kg of isosorbide flake from the package through a circular discharge hole with 20 cm diameter formed at the bottom of the package while tilting the package with the discharge hole to one side by 60° was measured.

3. Degree of caking: When the isosorbide flake packaged and stored under applied external force was filtered with a sieve of 50 mm×50 mm, the weight ratio of the isosorbide flake which could not pass through the sieve and remained on the sieve [i.e., the weight of isosorbide flake remaining on the sieve (kg)/the total weight of the packaged isosorbide flake (kg)*100%] was measured.

4. Amount of isosorbide flake having the major axis in a length of 5 mm or greater: In the production process of isosorbide flake, 100 g of isosorbide flakes after passing through the pulverizer was randomly sampled and spread on a graph paper (5 mm×5 mm), and examined by naked eye. After the examination, the amount (% by weight) of isosorbide flakes having the major axis in a length of 5 mm or greater was measured. Ten (10) samples in total per 500 kg of the prepared isosorbide flake were measured, and the average value thereof was described in Table 1.

As described in the above Table 1, in case of Examples 1 to 3 (i.e., isosorbide flakes with an average thickness of 0.5 to 4 mm wherein the amount of isosorbide flakes having the major axis in a length of 5 mm or greater was 90% by weight or more), the increase of the apparent specific gravity before/after applying external force was 0.2 or less, the isosorbide flakes were discharged completely even after applying external force, and the degree of caking after applying external force was 20% or less.

However, in case of Comparative Example 1 (i.e., isosorbide flakes with an average thickness of less than 0.5 mm wherein the amount of isosorbide flakes having the major axis in a length of 5 mm or greater was 90% by weight or more), the increase of the apparent specific gravity before/after applying external force was 0.26, it was impossible to measure the degree of retention after applying external force (i.e., discharging was impossible), and the degree of caking after applying external force was 64%.

In addition, in case of Comparative Example 2 (i.e., isosorbide with an average thickness of less than 0.5 mm wherein the amount of isosorbide having the major axis in a length of 5 mm or greater was less than 90% by weight), the increase of the apparent specific gravity before/after applying external force was 0.29, it was impossible to measure the degree of retention after applying external force (i.e., discharging was impossible), and the degree of caking after applying external force was 90% since the caking became severe after applying external force.

In addition, in case of Comparative Example 3 (i.e., isosorbide flakes with an average thickness of 1 mm wherein the amount of isosorbide flakes having the major axis in a length of 5 mm or greater was less than 90% by weight), the increase of the apparent specific gravity before/after applying external force was 0.22, it was impossible to measure the degree of retention after applying external force (i.e., discharging was impossible), and the degree of caking after applying external force was 44%.

As can be seen from the above, in case of isosorbide flakes with an average thickness of 0.5 to 4.5 mm wherein the amount of isosorbide flakes having the major axis in a length of 5 mm or greater was 90% by weight or more, the caking phenomenon occurring during long term storage is remarkably improved, and thus the flowability of the isosorbide flakes can be maintained in a good state.

The invention claimed is:

1. An anhydrosugar alcohol flake product which is a collective matter of plural anhydrosugar alcohol flakes, wherein the plural anhydrosugar alcohol flakes have an average thickness of from 0.8 mm to 4.5 mm, wherein the anhydrosugar alcohol flakes have an apparent specific gravity of 0.50 to 0.88 ton/m³, wherein 90% by weight or more of the anhydrosugar alcohol flakes have the major axis in a length of 5 mm or greater; and wherein the anhydrosugar alcohol flakes are isosorbide flakes.

2. The anhydrosugar alcohol flake product of claim 1, which has an apparent specific gravity of 0.50 to 0.8 ton/m³.

3. The anhydrosugar alcohol flake product of claim 1, which exhibits an increase of an apparent specific gravity of 0.2 or less according to applying external force, wherein said applying external force means packaging 500 kg of the anhydrosugar alcohol flake product and storing it outdoors at a daily mean temperature of from 21° C. to 26° C. for 100 days under applied external force by 500 kg load thereon.

4. The anhydrosugar alcohol flake product of claim 1, which exhibits an increase of the degree of retention of 5 minutes or less according to applying external force, wherein said degree of retention means the time taken for completely discharging 500 kg of the anhydrosugar alcohol flake product from the package through a circular discharge hole with 20 cm diameter formed at the bottom of the package while tilting the package with the discharge hole to one side by 60°, and wherein said applying external force means packaging 500 kg of the anhydrosugar alcohol flake product and storing it outdoors at a daily mean temperature of from 21° C. to 26° C. for 100 days under applied external force by 500 kg load thereon.

5. The anhydrosugar alcohol flake product of claim 1, which exhibits the degree of caking of 40% or less after applying external force, wherein said degree of caking is measured, when the anhydrosugar alcohol flake product is packaged and stored under applied external force and then filtered with a sieve of 50 mm×50 mm, and wherein the degree of caking is calculated as a percentage of the weight of anhydrosugar alcohol flake remaining on the sieve (kg) to the total weight of the packaged anhydrosugar alcohol flake (kg), and wherein said applying external force means packaging 500 kg of the anhydrosugar alcohol flake product and storing it outdoors at a daily mean temperature of from 21° C. to 26° C. for 100 days under applied external force by 500 kg load thereon.

6. A method of making an anhydrosugar alcohol flake product according to claim 1, comprising a plurality of anhydrosugar alcohol flakes, the method comprising: (1) feeding a liquid of melted anhydrosugar alcohol continuously to a cooling plate of a flaker; (2) cooling the liquid of melted anhydrosugar alcohol in the cooling plate into a sheet form while moving the cooling plate; (3) separating the cooled anhydrosugar alcohol in sheet form from the cooling plate by using a blade installed at the exit of the cooling plate; and (4) passing the separated anhydrosugar alcohol in sheet form through a pulverizer to obtain plural anhydrosugar alcohol flakes, wherein the plural anhydrosugar alcohol flakes have an average thickness of from 0.8 mm to 4.5 mm, wherein the anhydrosugar alcohol flakes have an apparent specific gravity of 0.50 to 0.88 ton/m$^3$, wherein 90% by weight or more of the anhydrosugar alcohol flakes have the major axis in a length of 5 mm or greater; and wherein the anhydrosugar alcohol flakes are isosorbide flakes.

7. The method of making an anhydrosugar alcohol flake product of claim 6, wherein the flaker is a disc type flaker, a drum type flaker or a belt type flaker.

8. The method of making an anhydrosugar alcohol flake product of claim 6, wherein the flow rate of the liquid of melted anhydrosugar alcohol fed to the cooling plate is within a range of from 50 to 150 kg/hr, the rotation speed of the cooling plate is within a range of from 1 to 2 rpm, the temperature of the cooling plate is within a range of from 1 to 25° C., and the rotation speed of the pulverizer is within a range of from 100 to 300 rpm.

* * * * *